(12) United States Patent
Huang et al.

(10) Patent No.: US 8,772,321 B2
(45) Date of Patent: Jul. 8, 2014

(54) HETEROANNELATED ANTHRAQUINONE DERIVATIVES FOR INHIBITING CANCERS

(75) Inventors: Hsu-Shan Huang, Taipei (TW);
Tsung-Chih Chen, Taipei (TW);
Tai-Lung Cha, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 13/325,852

(22) Filed: Dec. 14, 2011

(65) Prior Publication Data

US 2012/0122937 A1    May 17, 2012

Related U.S. Application Data

(63) Continuation-in-part of application No. 12/193,564, filed on Aug. 18, 2008, now abandoned.

(30) Foreign Application Priority Data

Apr. 2, 2008 (TW) ............................... 97112087 A

(51) Int. Cl.
*A61K 31/428* (2006.01)
*C07D 285/14* (2006.01)

(52) U.S. Cl.
CPC .................... *C07D 285/14* (2013.01)
USPC ......................... 514/361; 548/126

(58) Field of Classification Search
CPC ........................... A61K 31/428; C07D 285/14
USPC .......................................... 514/361; 548/126
See application file for complete search history.

(56) References Cited

PUBLICATIONS

Hackam, et al. JAMA, 296(14), 2006, 1731-1732.*
Jordan, V. C. Nature Reviews: Drug Discovery, 2, 2003, 205.*
Klimasenko et al., Journal of Structural Chemistry (Zhurnal Strukturnoi Khimii),14(1), 1973, 108-115.

* cited by examiner

*Primary Examiner* — Douglas M Willis
(74) *Attorney, Agent, or Firm* — Muncy, Geissler, Olds & Lowe, P.C.

(57) ABSTRACT

Methods and pharmaceutical compositions for treating cancer utilizing compounds characterized by the following structure:

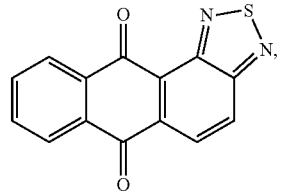

and their pharmaceutically acceptable salts.

11 Claims, 22 Drawing Sheets

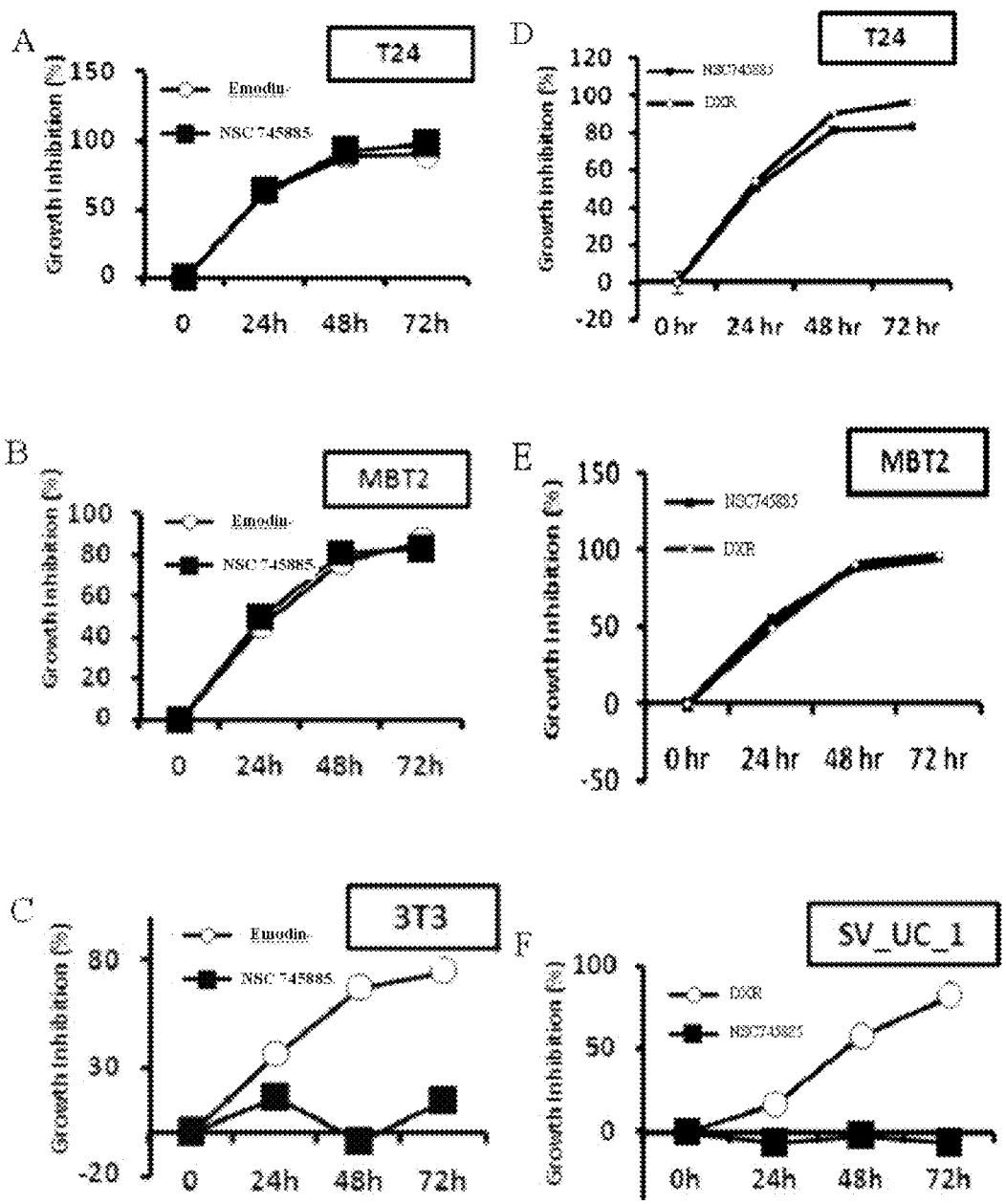
Fig. 9A ~Fig. 9F

HETEROANNELATED ANTHRAQUINONE DERIVATIVES FOR INHIBITING CANCERS

CROSS-REFERENCE TO RELATED APPLICATIONS

This application is a continuation-in-part of U.S. patent application Ser. No. 12/193,564 filed on Aug. 18, 2008 now abandoned, and claims benefit to this earlier filed application under 35 U.S.C. §120. This application also claims foreign priority under 35 U.S.C. §119 to Taiwanese Patent Application No. 97112087 filed in Taiwan on Apr. 2, 2008. The entire contents of all earlier filed applications are hereby incorporated by reference.

FIELD OF THE INVENTION

The present invention relates to heteroannelated anthraquinone derivatives and their use in treating cancers, and in particular their use in methods for inducing apoptosis, inhibiting telomerase activity and inhibiting abnormal cellular proliferation in living cells, tissues and organs.

BACKGROUND OF THE INVENTION

Apoptosis, also called the process of programmed cell death, is thought to play an important role in anticancer therapy. Strategies of inducing apoptosis as well as inhibiting abnormal cell proliferation are developed for anti-cancer therapy. Doxorubicin (DXR), one of the most well-known anti-cancer agents, could induce apoptosis in rat hepatoma cells (AH66). After 24 h of drug treatment, DNA fragmentation of the cells was observed within 15 h, along with an increase in caspase-3 activity. Intracellular caspase-3 activity is thought to be correlated well with the ability to induce DNA fragmentation (Asakura et al., Br. J. Cancer 1999, 80, 711-715).

A telomere is a region of repetitive DNA sequence at the end of a chromosome that protects the end of the chromosome from deterioration or fusion with neighboring chromosomes. In normal somatic cells, telomeres become shortened each time the cells divide via mitosis. There is growing evidence that accelerated telomere attrition and/or aberrant telomerase activity contribute(s) to pathogenesis in a number of diseases and may also increase cellular survival by conferring resistance to apoptosis (Bermudez et al., Clin. Interv. Aging 2006, 1, 155-167). Furthermore, the expression of human telomerase reverse transcriptase (hTERT) reduces activation of caspases 3, 8, and 9, reduces pro-apoptotic mitochondrial proteins t-BID, BAD, and BAX and increases anti-apoptotic mitochondrial protein, Bcl-2. The ability of telomerase to suppress caspase-mediated apoptosis is p-JNK-dependent since abrogation of JNK expression with JIP abolishes resistance to apoptosis. Reductions in hTERT mRNA expression level and telomerase activity are observed during the processes of cellular aging or immortalization (Bestilny et al., Cancer Res. 1996, 56, 3796-802). Still, the level of telomerase activity in somatic cells, which is undetectable at the basal level, could be heightened by induction of hTERT cDNA (Bodnar et al., Science. 1998, 279, 349-52).

Telomeres in eukaryotic cells are guanine-rich. Under normal physiological conditions, single-strand DNA of the telomeres will spontaneously form a G-quadruplex structure. The G-quadruplex structure includes two portions in which one is a small loop composed of TTA, and the other a guanine-tetrad composed of four guanines formed by cyclic hydrogen bonds. Because of the role telomerase plays in cellular aging and apoptosis, direct inhibition of telomerase activity can be used to block the differentiation of tumor cells. Similarly, stabilizing the G-quadruplex structure to inhibit its complementation with the single strand RNA (AAUCCC) can also prevent telomere extension, thereby inhibiting cell proliferation. In short, inhibition of chromosome replication via either inhibition of telomerase or stabilization of the G-quadruplex offers a potential strategy for inhibiting tumor cell growth (Smogorzewska et al., Annu. Rev. Biochem. 2004, 73, 177-208).

Induction of apoptosis or inhibition of telomerase activity by anti-cancer agents has been shown to correlate with tumor suppression; however, non-apoptotic forms of cell death, such as autophagy and extrinsic senescence, have also been shown to contribute to the overall tumor response. Cellular damage induces growth arrest and tumor suppression by inducing apoptosis, necrosis, senescence and the expression of p53; the mechanism of cell death depends on the magnitude of DNA damage following exposure to various concentrations of anti-cancer agents. p53 is a transcription factor that activates vital damage containment procedures to restrict aberrant cell growth in response to DNA damage, oncogene activation, hypoxia and the loss of normal cell contacts (Giaccia and Kastan, Denes Dev. 1998, 12, 2973-2983; Lohrum and Vousden, Cell Death Differ. 1999, 6, 1162-1168). p53 restricts cellular growth not only by inducing a non-apoptotic mechanisms involved in senescence, cell cycle arrest (at G1 and/or G2 phase) but also by inducing apoptotic mechanisms (Jin and Levine, J. Cell Sci. 2001, 114, 4120-4139). p53 is also reported to be able to work coordination with p21 for noscapine-mediated apoptosis (Aneja et al., Cancer Res. 2007, 67, 3862-3870). In addition, Apoptosis-resistant cells and transduction pathways which inhibit apoptosis can induce non-apoptotic mechanisms of cell death and senescence, thereby preserving the antitumor effect of some anti-cancer agents (Kim et al., Cancer Biol. Ther. 2006 11, 1429-1442), implicating a potentially-flexible strategy for inhibiting cancer cell proliferation and inducing apoptosis.

It is known that over-expression of known oncogenes usually induces cancers. It is also known that over-expression of these genes is also associated with many cell proliferation disorders, such as chronic lymphocytic leukemia, esophagus cancer, myeloma, etc. Moreover, many experiments have shown that over-expression of tumor suppressor genes can play an important role in the prevention and treatment of tumors, thereby, establishing the connection between cancer and cell proliferation disorders. Therefore, research and development on drugs for curing cell proliferation disorders, such as telomerase inhibitors, can be applied to the treatment of human cancers, as taught in the disclosures of Canadian Patent No. 2,428,206.

Although quite a few strategies associated with inducing apoptosis and inhibiting cell proliferation via telomerase inhibition could be surmised based on the foregoing knowledge, no report has been made to date for any substances with unambiguously effective said strategies and properties satisfactory for pharmaceutical use.

SUMMARY OF THE INVENTION

Accordingly, it is one object of the present invention to provide a pharmaceutical that is capable of inducing cell apoptosis and inhibiting telomerase activity and cell proliferation in cells, particularly preneoplastic, neoplastic, transformed, tumorigenic, premetastatic, metastatic and cancer cells.

It is another object of the present invention to provide a method for inducing cell apoptosis and inhibiting or curtailing cell proliferation in cells that exhibit cellular proliferation disorders, particularly cancer cells.

It is yet another object of the invention to provide a pharmaceutical composition for treating cell proliferation disorders, particularly cancer.

These objects are satisfied by the unexpected discovery that the compound anthra[2,1-c][1,2,5]thiadiazole-6,11-dione (NSC745885, formula (I)) is an effective cancer inhibitor.

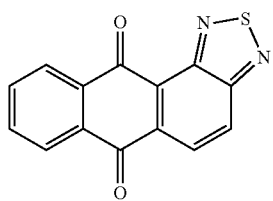

(I)

Therefore, in one aspect, the present invention provides methods for inhibiting telomerase activity, inhibiting cell proliferation and inducing cell apoptosis in a cell. Embodiments in accordance with this aspect of the invention generally include the step of exposing the living cell to anthra[2,1-c][1,2,5]thiadiazole-6,11-dione (NSC745885).

In another aspect, the present invention also provides a pharmaceutical composition useful for treating cell proliferation disorder or cancer by inducing cell apoptosis and inhibiting cell proliferation. Embodiments in accordance with this aspect of the invention will generally comprise a pharmaceutical composition that includes a compound of

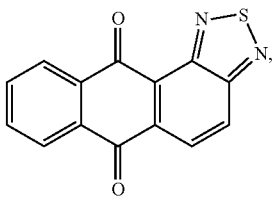 [SMILES: O=C1c2ccccc2C(=O)c2c1ccc1nsnc21]

(I)

or a pharmaceutically acceptable salt thereof and a pharmaceutically acceptable carrier, vehicle or solvent. The pharmaceutical composition further comprises a diluent, an excipient, at least one solvent, at least one buffer, and optionally one or more pharmaceutically acceptable excipients independently selected from the group consisting of preservatives and surfactants. Compositions of the invention, the salts preferably are base addition salts. Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, Nbutylamine, ethylene diamine, ethanolamine, and choline, and salts with amino acids such as arginine, lysine, and so forth.

Cells to be treated by methods or compositions of the present invention are preferably cancer cells. Exemplary cancer cells may include a lung cancer cell, hepatic cancer cell, pancreatic cancer cell, bladder cancer cell, brain cancer cell, stomach cancer cell, colon cancer cell, breast cancer cell, prostate cancer cell, kidney cancer cell, oral cancer cell, cervical cancer cell and ovary cancer cell, but are not limited thereto.

Additional aspects and advantages of the invention will be set forth in the following description and the appended claims, but are not limited thereto.

BRIEF DESCRIPTION OF THE DRAWINGS

FIG. 4 shows an exemplary result of NSC745885-induced cell apoptosis in HeLa cell. FIG. 5 shows NSC745885-induced cellular autophagy and senescence in HeLa cell.

FIG. 6 shows an exemplary immunoblot result of p53 and p21 expression induced by NSC745885.

FIG. 7 shows NSC745885 interacting with Zac1 in the regulation of p53-dependent activation in HeLa cell.

FIG. 9A~FIG. 9F shows the cell proliferation inhibitory effect of NSC745885 in bladder cancer cell lines and other cell lines. The bladder cancer cell lines includes T24 (FIG. 9A, 9D) and MBT2 (FIG. 9B, 9E). the non-cancer cell fibroblast 3T3 (FIG. 9C) and normal epithelial cell SV_UC_1 (FIG. 9F).

FIG. 10 Panel A shows the SCF protein expression was suppressed in bladder cancer cell (MBT2, T24) and normal epithelial cell (SV_HUC_1) by NSC74588. FIG. 10 Panel B shows that NSC745885 down-regulates oncogenic SCF protein expression in many other cancer cells.

DETAILED DESCRIPTION OF THE INVENTION

Figure 1:
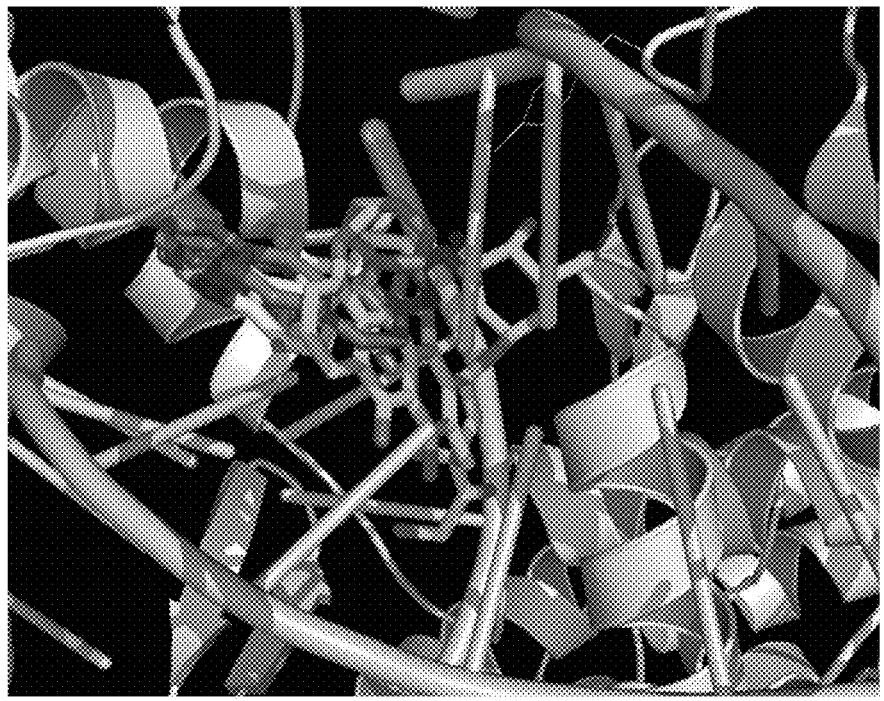
FIG. 1 shows an exemplary docked structure of DXR (doxorubicin) and NSC745885 in the type IIA topoisomerase active site.

The present invention will now be described more fully with the aid of experiment results of the following exemplary embodiments. It is to be noted that the following descriptions of exemplary embodiments of this invention are presented herein for the purposes of illustration and description only; they are not intended to be exhaustive, nor shall they be construed as limiting.

Exemplary methods for manufacturing the heteroannelated anthraquinone derivative in accordance with embodiments of the present invention will generally include cyclization and condensation reactions. As used in this disclosure, the terminology "pharmaceutical composition" can be interpreted to mean a chemical composition intended for and/or capable of inducing or affecting a change in the chemical makeup (e.g., genome, transcriptome, proteome, lipidome and/or metabolome), biological activity or phenotype of a living cell, tissue, organ or organism, or a change in the chemical activity of a biological enzyme. The terminology "biologically active amount" can be interpreted to mean any amount of a substance that is able to induce or affect a change in the chemical makeup, biological activity or phenotype of a living cell, tissue, organ or organism, or a change in the chemical activity of a biological enzyme. Other interpretations of this terminology will be known to those of skill in the art.

Embodiment 1: The Synthesis Process of Compound of Formula (I) (Anthra[2,1-c][1,2,5]thiadiazole-6,11-dione) (NSC745885)

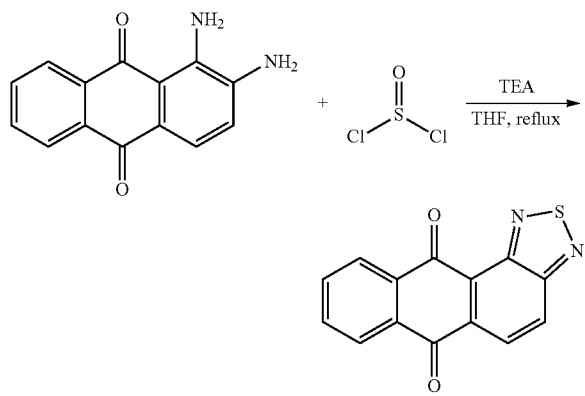

The compound 1,2-Diaminoanthraquinone (1.19 g, 5 mmol) is dissolved in THF (30 mL), and thionyl chloride (0.15 g, 20 mmol) is then dripped thereinto; triethylamine (TEA, 3 mL) is lastly added thereinto for catalyzation. After being mixed at room temperature for one hour, the mixture is transferred into a container with 200 mL of icy water for crystallization. After filtration, a precipitate is collected and re-crystallized with hot alcohol, so as to obtain the yellow compound NSC745885 with a melting point of 227-228° C., and the production rate is about 74%.

NSC745885 synthesized via the above process has the following characteristics: MW 266.0150 ($C_{14}H_6N_2O_2S$); $R_f$: 0.8 (ethyl acetate:dichloromethane=1:4); IR (KBr) cm$^{-1}$: 1671(CO); EI-MS m/z: 210(57%), 238(64%), 266(M$^+$, 100%), HRMS (ESI-TOF) m/z: calcd for $C_{14}H_7N_2O_2S^+$ [M+H]$^+$: 267.0223. found: 267.0226; 1H-NMR (300 MHz, CDCl$_3$) δ (ppm): δ7.84(1H, dd, J=12.15,6.9 Hz, Ar—H$_7$), δ7.85(1H, dd,J=13.2,7.5 Hz, Ar—H$_{10}$), δ8.33(1H, dd, J=22.5, 7.2 Hz, Ar—H$_8$), δ8.33(1H, dd, J=22.5, 7.2 Hz, Ar—H$_9$), δ8.41(1H, d, J=9.3 Hz, Ar—H$_5$), δ8.56(1H, d, J=9.3 Hz, Ar—H$_4$); and 13C-NMR (75 MHz, CDCl$_3$) δ (ppm): 125.07, 126.35, 126.99, 127.34, 127.61, 132.08, 133.47, 134.15, 134.75, 135.16, 150.93, 157.99, 181.97 (CO), 183.31(CO).

NSC745885's physical characteristics are confirmed via the following mechanism. Melting points were determined with a Buchi B-545 melting point apparatus and are uncorrected. All reactions were monitored by TLC (Silica Gel 60 F254). $^1$H NMR: Varian GEMINI-300 (300 MHz) and Brucker AM-500 (500 MHz); d values are in ppm relative to TMS as an internal standard. Fourier-transform IR spectra (KBr): Perkin-Elmer 983G spectrometer. Mass spectra (EI, 70 eV, unless otherwise stated): Finnigan MAT TSQ-46, Finnigan MAT TSQ-700 (Universitat Regensburg, Germany) and Finnigan MAT LCQ-MS (National Research Institute of Chinese Medicine, Taipei, Taiwan). Typical experiments illustrating the general procedures for the preparation of the anthraquinones are described below.

Embodiment 2: Docked Structures of NSC745887 in the Type IIA Topoisomerase Active Site Docking the structures of NSC745887 in the type IIA topoisomerase active site. The type IIA topoisomerase involves hydroxyl oxygens of conserved tyrosine residues in the active site of the topoisomerase at the central region of the DNA gate, which act to pull the DNA away from a continuous DNA backbone trajectory. The docking of the compound NSC745887 and the anthracyclin antibiotic agent doxorubicin (DXR) into type IIA topoisomerase were performed using the protocol of Dock Ligand (LibDock) (Receptor-Ligand Interactions module in Accelrys Discovery Studio 2.1, Accelrys Inc). The structures of Streptococcus pneumonia topoisomerase IV in complex with DNA and in complex with moxifloxacin (PDB code: 3FOF) were used as the receptor structure, and the binding site of moxifloxacin was defined as the site sphere. Scoring functions of LigScor1, LigScor2, PLP1, PLP2, PMF, PMF04 and Jain were adopted upon docking. The resulting docking poses were subjected to in situ minimization in the presence of the receptor using the Ligand Minimization protocol. Optimization of residue geometry for the binding poses with the highest consensus score was done using the Minimization in Simulation module protocol with the algorithm of smart minimization until the gradient tolerance was satisfied. The binding energy for the compounds was calculated using the Calculate Binding Energy in Receptor-Ligand Interactions module. Referring to FIG. 1, the structures of the protein complexes are presented in stick and ribbon representation. Protein and DNA are shown as ribbon models. NSC745887 and DXR are shown as stick models respectively.

The Following Embodiments 3~9 are Practiced in HeLa Cells.

Embodiment 3: DNA Damage in HeLa Cell

Figure 2:
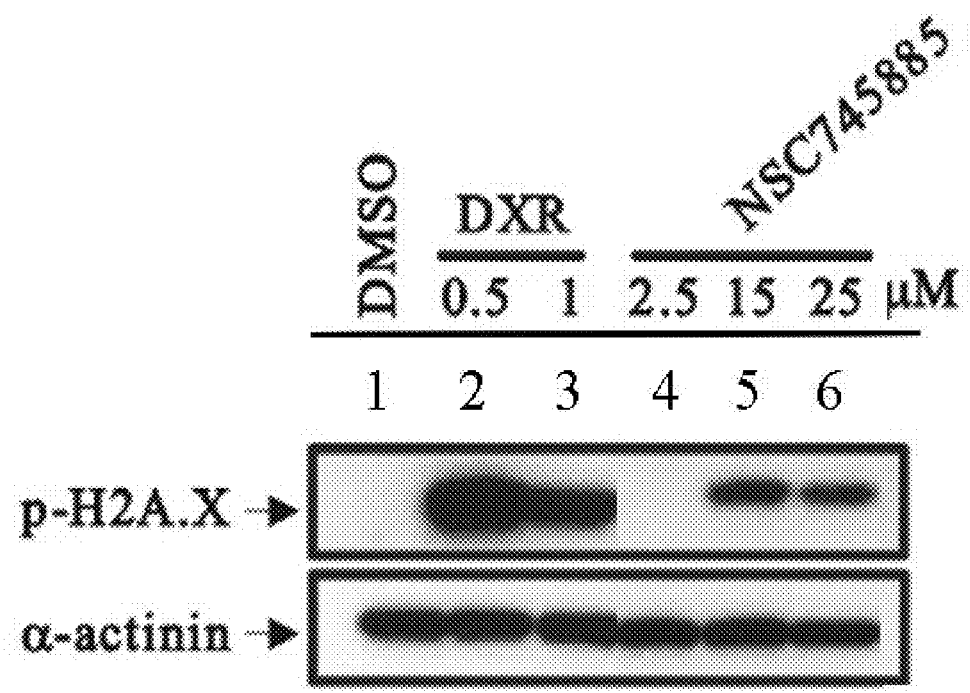
FIG. 2 shows an exemplary immunoblot result of phosphorylated γ-H2A.X in NSC745885 and DXR treated HeLa cells.

The anthracyclin antibiotic agent doxorubicin (DXR) is an active cytotoxic reagent with a wide range of clinical indications, including treatment of solid tumors in the ovary, breast, and gastrointestinal systems, as well as treatment of liquid tumors such as leukemia. As shown in FIG. 2, the induction of DNA damage by DXR and NSC745887 was assessed by immunoblot analysis of γ-phosphorylation of histone H2A.X at serine residue 139. Specifically, HeLa cells were treated with NSC745885 at various doses for 12 hour. The phosphorylation of γ-H2A.X was subsequently detected by the immunoblot. The assay indicates that similar to DXR, NSC745885 strongly induced DNA damage in HeLa cells.

Embodiment 4: NSC745885 Caused Changes in Cell Cycle Profile of HeLa Cell

Figure 3:
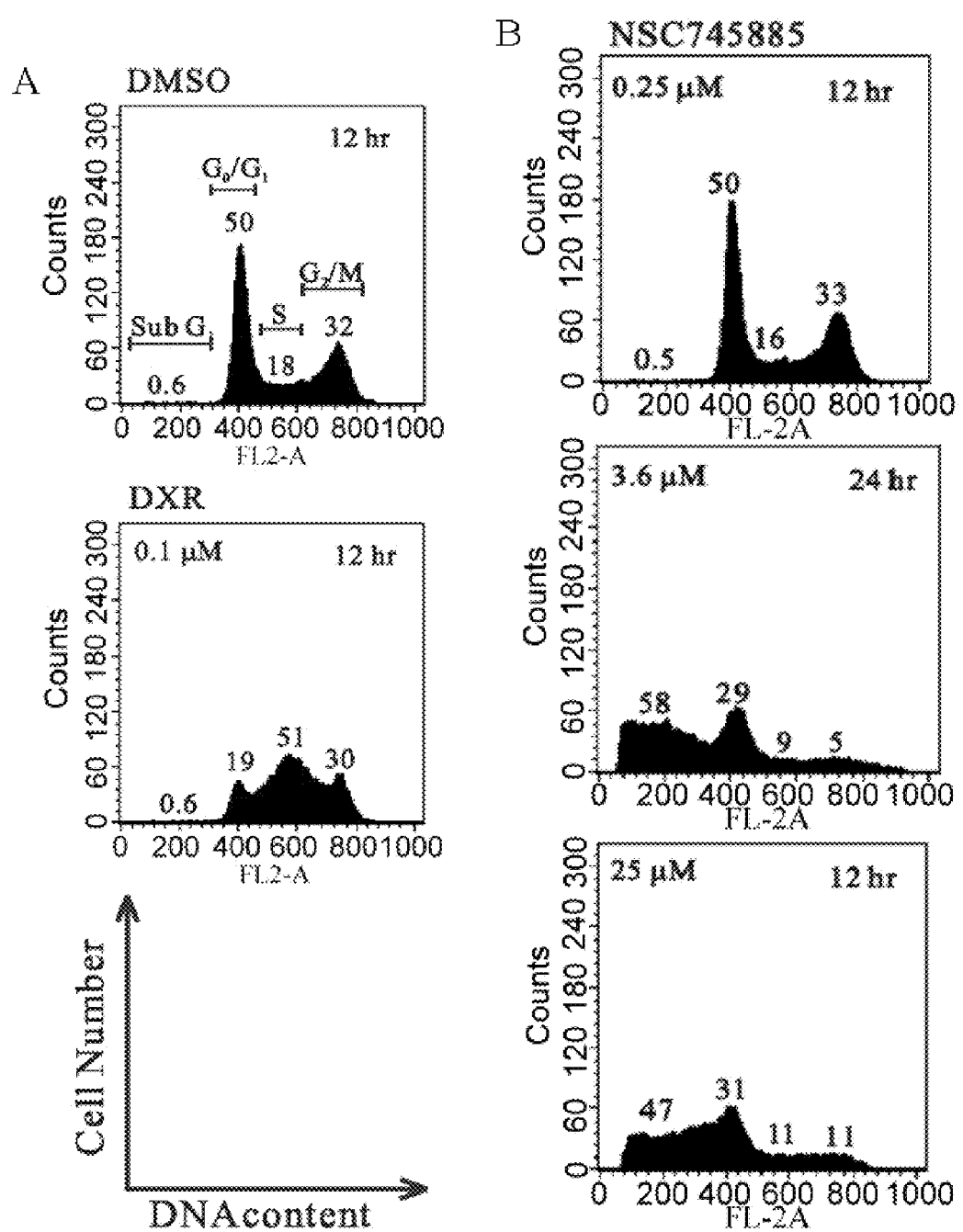
FIG. 3 (Panels A & B) shows the effect of NSC745885 in cell cycle profile of HeLa cell.

Cell cycle arrest is an important damage surveillance mechanism. When we evaluated the effect of the compounds on cell cycle progression using FACS, it was found that DXR induced cell cycle arrest in S phase (FIG. 3, Panel A). Treating the cells with NSC745885 caused 47-58% of cells to arrest in sub-G1, which is indicative of cell death. This effect was dose- and time-dependent (FIG. 3, Panel B). Longer treatment or treatment with higher concentrations of NSC745885 resulted in more cells with sub-G1 DNA content.

Embodiment 5: NSC745885 Induces Cell Apoptosis in HeLa Cell

Figure 4A:
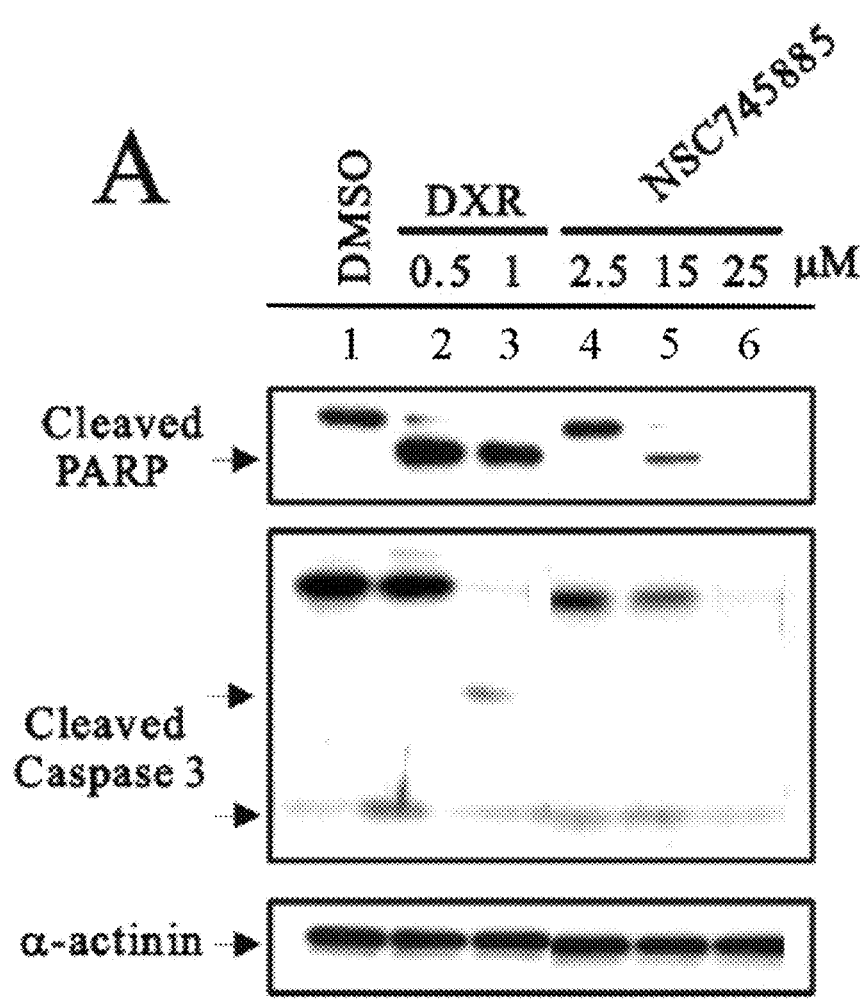
FIG. 4A shows the immunoblot of cleaved PARP and caspase 3 as apoptotic indicators and DXR as a positive control.
Figure 4B:
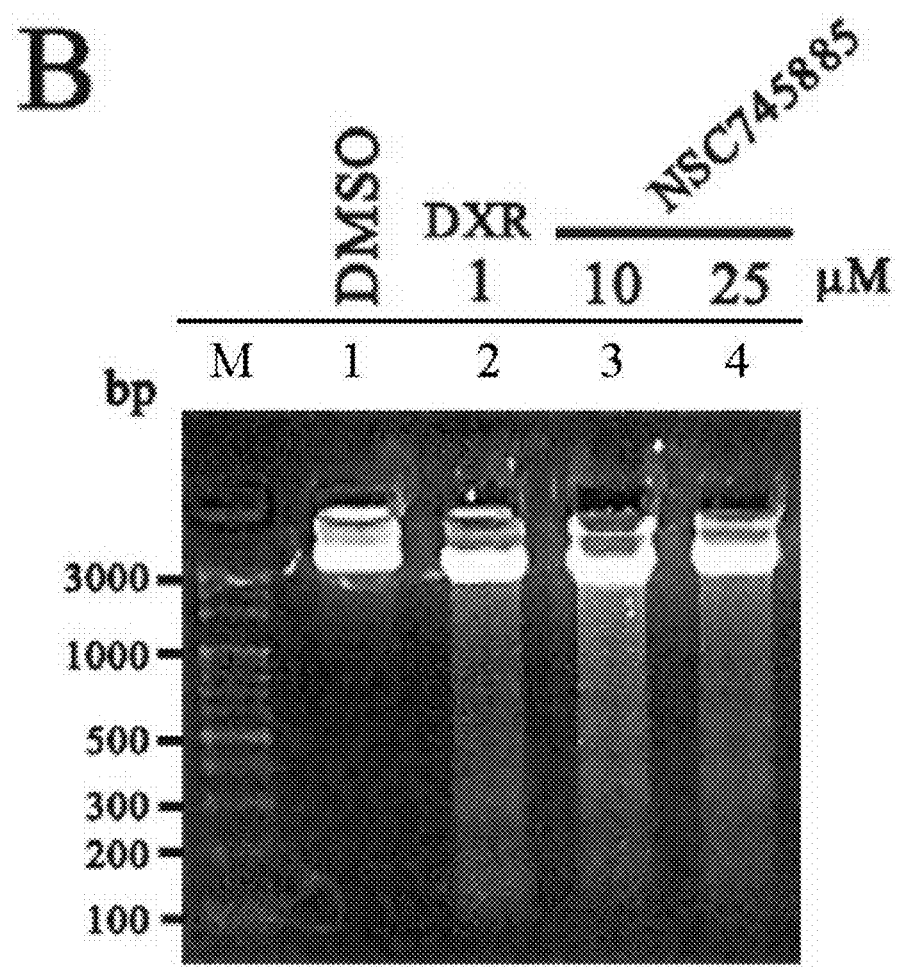
FIG. 4B shows agarose gel electrophoresis of DNA fragmentation as an apoptotic indicator and DXR as a positive control

It is well noted that DXR can induce cardiomyocyte death by apoptosis and necrosis. DXR is also involved in other types of cellular processes, such as autophagy and senescence/aging. To investigate induction of apoptosis caused by NSC745885, we adopted DXR as a positive control and examined the levels of cleaved PARP and caspase 3 as apoptotic indicators using immunoblot (FIG. 4A), as well as DNA fragmentation using agarose gel electrophoresis (FIG. 4B). HeLa cells were treated with either DXR or NSC745885 at various doses for 16 hours. Subsequently, the total cellular protein was extracted and immunoblotted with antibodies against the cleaved types of PARP and caspase 3. Additionally, genomic DNA was isolated and analyzed by 2% agarose gel electrophoresis followed by ethidium bromide staining. The results (FIG. 4A and FIG. 4B) are representative of three independent experiments. Apoptosis was strongly induced by DXR (FIG. 4A, compare lanes 1-3 and FIG. 4B, compare lanes 1 and 2). NSC745885 had a comparable effect on HeLa cell apoptosis (FIG. 4A, compare lanes 4-6 and FIG. 4B, compare lanes 3-4). Intriguingly, the protein levels of cleaved PARP and caspase 3 were dramatically decreased when HeLa cells were treated with a high concentration of NSC745885 (25 μM) compared to DXR (FIG. 4A compare lanes 1-3 and 4-6). Treatment with NSC745885 decreased protein stability, an effect that appeared to be selective, and was confirmed in other immunoblot analyses (shown in FIG. 6A, lanes 1 and 6).

Embodiment 6: NSC745885 Induces Cellular Autophagy and Senescence

Cell lysates were prepared in lysis buffer (100 mM Tris-HCl pH 8.0, 150 mM NaCl, 0.1% SDS, and 1% Triton 100) at 4° C., separated by sodium dodecyl sulfate-polyacrylamide gel electrophoresis (SDS-PAGE), and then transferred onto a polyvinylidine difluoride membrane (Millipore, USA). Proteins were detected using antibodies against alpha actinin (ACTN), proliferating cell nuclear antigen (PCNA), p53, p21, cyclin B1, and cyclin D1 (Santa Cruz Biotechnology, USA), YH2A.X (EP854(2)Y, Epitomics, USA), cleaved caspase 3, cleaved poly(ADP-ribose) polymerase (PARP) and LC3B-II (Cell signaling, USA).

Altered intracellular localization of LC3B (LC3B-I) and increased electrophoretic mobility of LC3B (LC3B-II) are correlated with recruitment to autophagic membranes and can be used as molecular markers for autophagic activation. Treatment of HeLa cells with DXR or NSC745885 resulted in drug-induced LC3B-II fragment formation, as measured by immunoblot (FIG. 5A, compare lanes 2 and 3 for DXR; lanes 4-6 for NSC745885).

Figure 5A:
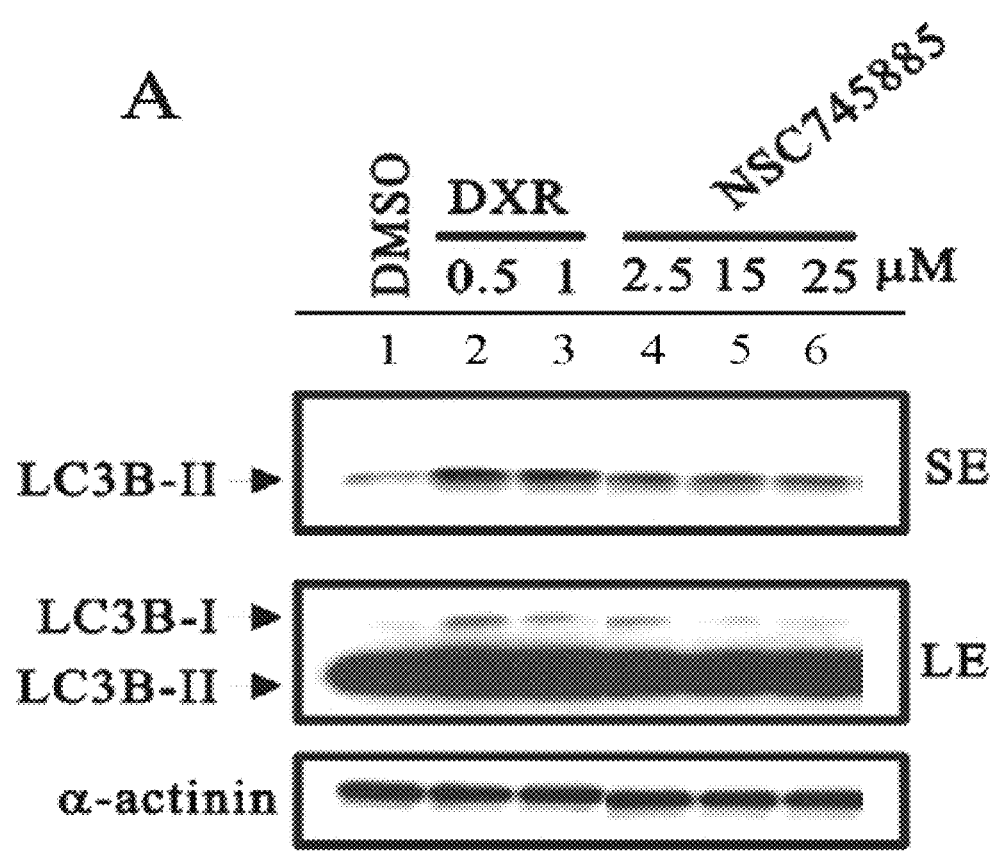
FIG. 5A shows NSC745885-induced LC3B-II fragment formation measured by immunoblot.

In FIG. 5A, HeLa cells were treated with the indicated concentrations of DXR, NSC745885 for 12 hours, and then cell lysates were analyzed by immunoblot using antibodies directed against LC3. The results are representative of three independent experiments.

Figure 5B:
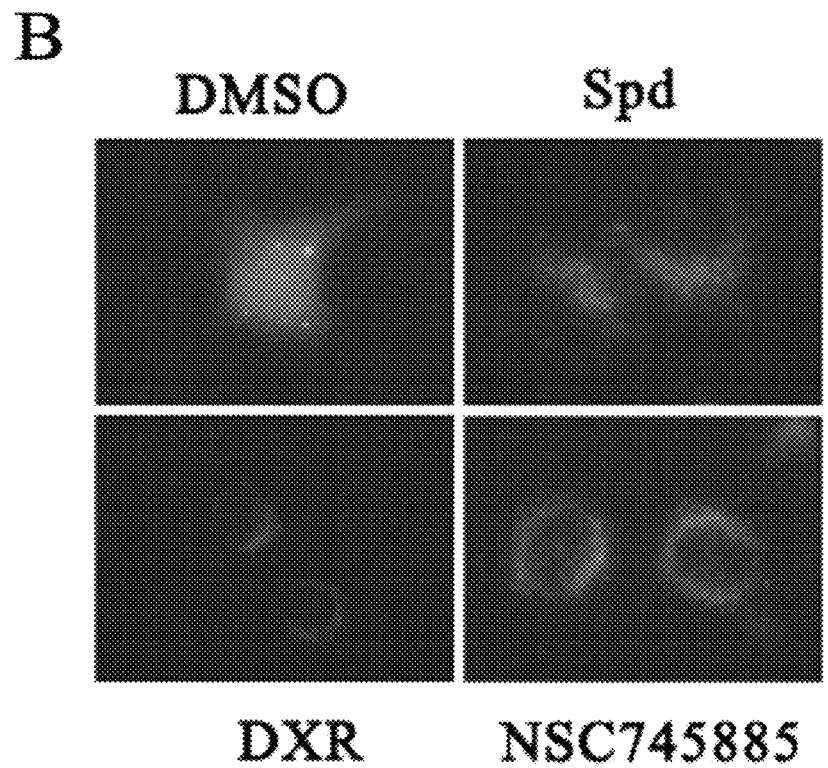
FIG. 5B shows a marker of autophagosome formation monitored with fluorescence microscopy.

In FIG. 5B, HeLa cells were transfected with 0.25 μg of an expression vector for GFP-LC3 for 24 hours and then treated with 2.5 μM NSC745885 for 12 hours. GFP-LC3, a marker of autophagosome formation, was monitored with fluorescence microscopy. Autophagosome formation as indicated by LC3 aggregation was observed in HeLa cells treated with DXR as well as the three anthraquinones. Vehicle (DMSO) and spermidine (Spd) were used as a negative and positive control, respectively.

The in situ Staining for Senescence-associated (SA) β-galactosidase Activity.

Cultured cells were washed in PBS (pH 7.4), incubated in a solution of 2% formaldehyde/0.2% glutaraldehyde, and then incubated overnight at 37° C. in freshly prepared staining solution consisting of 1 mg/mL X-gal (5-bromo-4-chloro-3-indolyl-β-D-galactoside), 5 mM $K_3Fe(CN)_6$, 5 mM $K_4Fe(CN)_6$, 150 mM NaCl and 2 mM $MgCl_2$ in 40 mM citric acid/sodium phosphate, pH 6.0. Following this incubation, cells were washed with water and examined by light microscopy at 200× magnification.

Figure 5C:
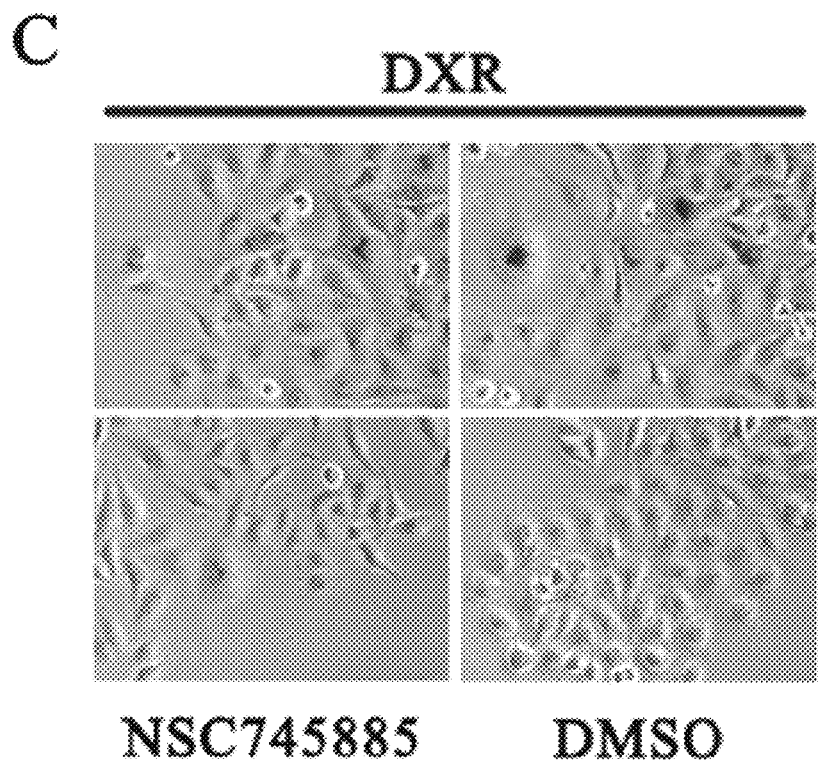
FIG. 5C shows cells that are subjected to SA-β-galactosidase staining
Figure 5D:
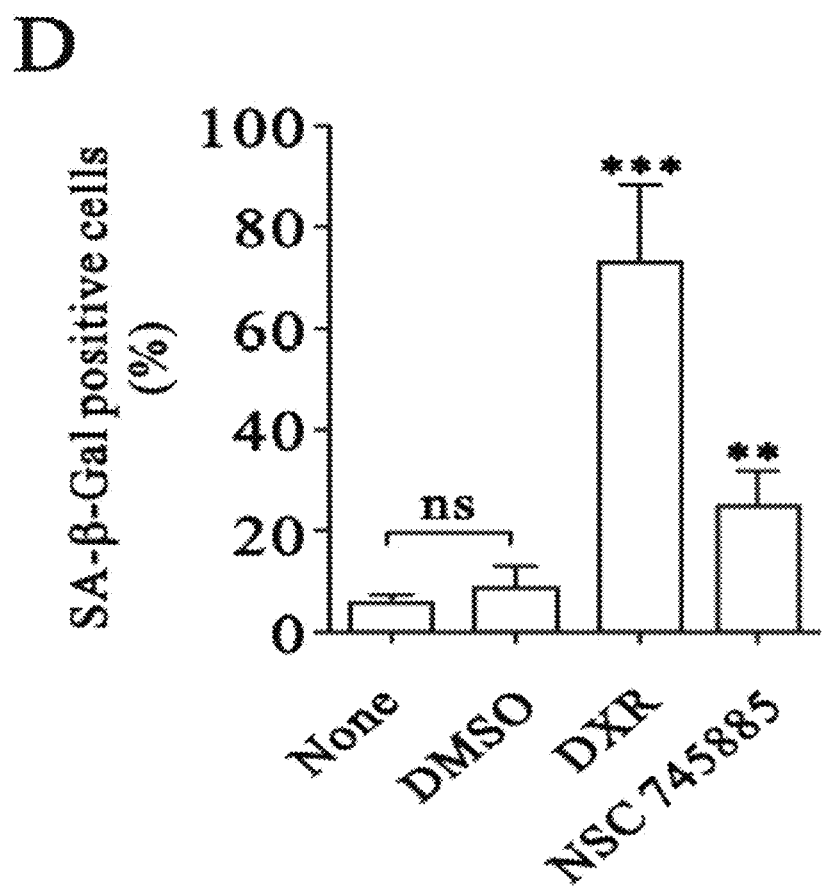
FIG. 5D shows approximately 100 stained cells that are quantified.

In FIGS. 5C and 5D, HeLa cells were incubated with 2.5 μM NSC745885 for 24 hours. After 48 hours, cells were subjected to SA-β-galactosidase staining (FIG. 5C) and approximately 100 stained cells were quantified (*P<0.05;  P<0.01; * P<0.005). NSC745885 induced senescence at a rate of 25% (P=0.0085 compared to DMSO). (FIG. 5D) LC3B-I fragments were observed when the cells were exposed to the drug for longer period of time (FIG. 5A, panel labeled as LE). Upon transient transfection of an expression vector for a fluorescent LC3 fusion protein, GFP-LC3, autophagosome formation (as indicated by LC3 aggregation) was observed in HeLa cells treated with DXR or N745885 (FIG. 5B). We also treated Hela cells with the autophagy inducer spermidine (Spd) and vehicle (DMSO), which act as the positive and the negative control, respectively. Consistent with the previous assays, DXR was found to induce cell senescence at low concentrations compared to DMSO (73% versus 9%), as measured by SA-β-galactosidase staining (FIGS. 5C and D, compare DMSO and DXR; P=0.0002). NSC745885 was found to induce senescence at a rate of 25% (P=0.0085 compared with DMSO).

Embodiment 7: p53 and p21 Expression Induced by NSC745885

Cell cycle regulatory protein p21 is one of p53's targets. Previous studies showed that p53 protein expression is increased by DXR in a concentration-dependent manner; however, p21 is induced by DXR at lower concentrations but decreased at higher concentrations. In this experiment, HeLa cells were treated with the indicated concentrations of DXR or NSC745885 for 12 hours and then assessed by immunoblot (FIG. 6A) and RT-PCR (FIG. 6B).

Figure 6A:
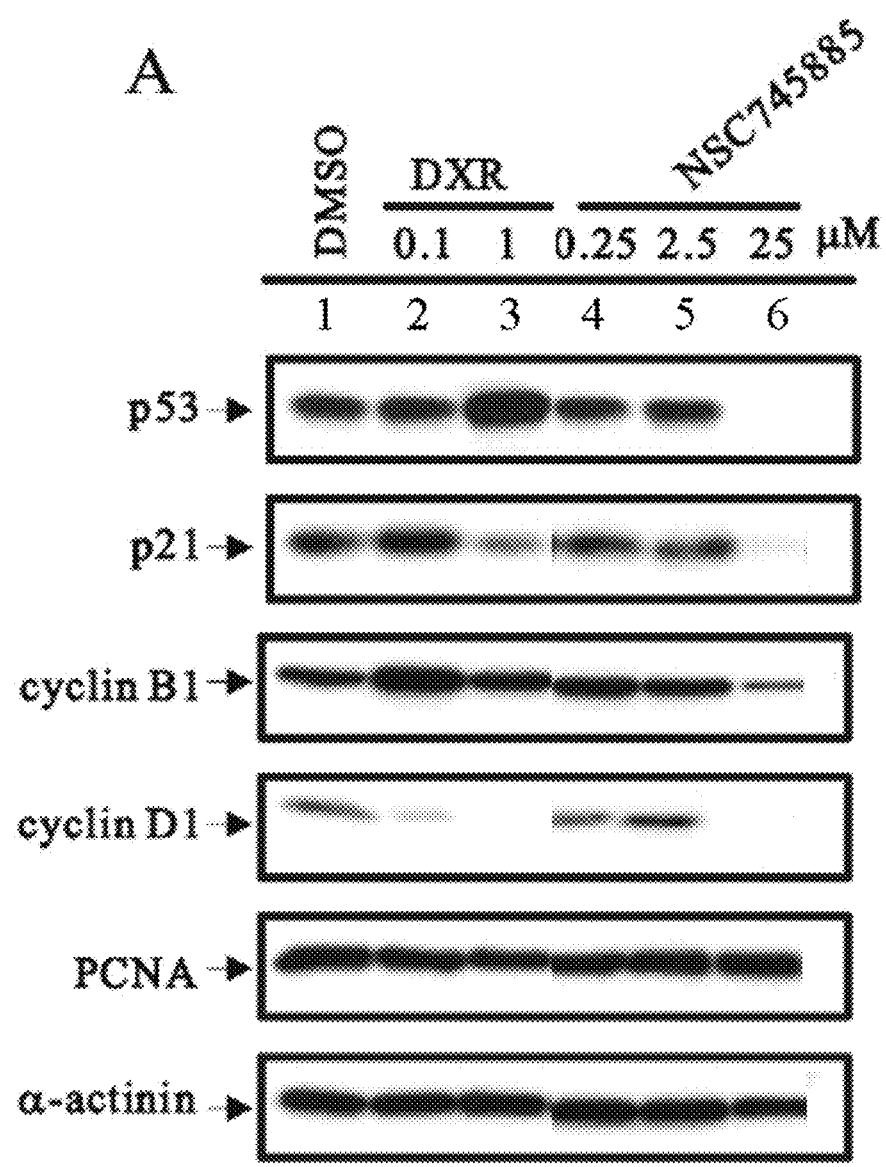
FIG. 6A shows immunoblot of p53 and p21.
Figure 6B:
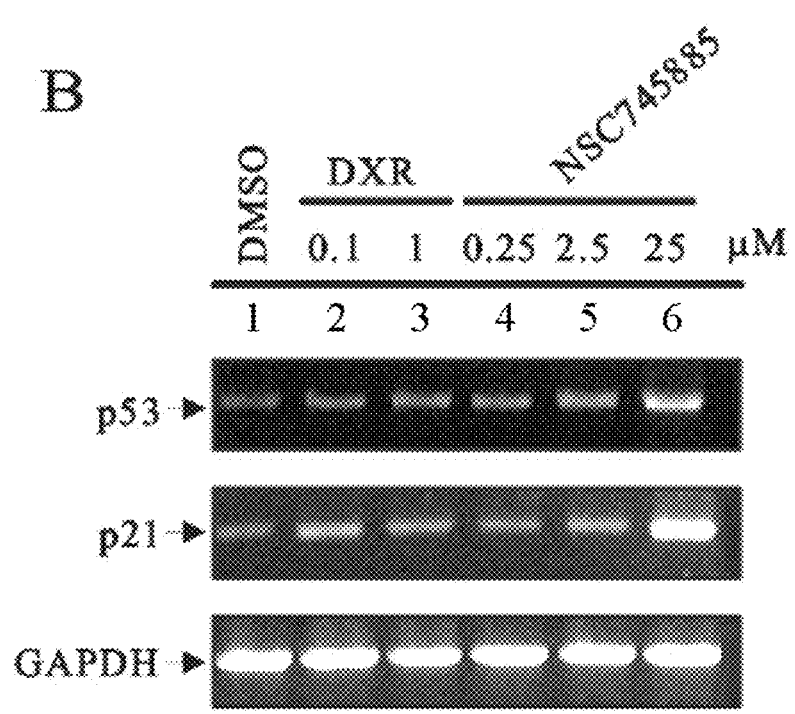
FIG. 6B shows RT-PCR p53 and p21.

In DXR-treated HeLa cells, immunoblot analysis indicates that p21 was regulated probably via both p53-dependent and p53-independent mechanisms (FIG. 6A, compare lanes 1-3). In contrast, NSC745885 decreased p21 as well as p53 in a concentration-dependent manner (FIG. 6A, compare lanes 4-6). Levels of PCNA as well as the control protein ACTN remained constant under all treatment conditions; however, all other proteins, particularly p53 and p21, were decreased by 25 μM NSC745885 (FIG. 6A). To determine whether these effects on protein expression were occurring at the transcriptional or translational level, we examined mRNA expression levels with RT-PCR assay. Surprisingly, NSC745885 seemed to slightly increase p53 and p21 mRNA expression levels (FIG. 6B, lanes 4-6). Expression of p21 correlates with activation of p53 at low DXR concentration, but not at high concentrations. The 1,2-heteroannelated anthraquinones NSC745885 induced DNA damage compared to DXR, which could be responsible for driving cells to undergo apoptosis, autophagy, or senescence. The effects of the compounds on enhancing p53 protein stability at low concentration was transient, and two of NSC745885 induced marked p53 protein degradation at higher concentrations. In addition, the current data suggest that p53 is not the only protein degraded via an as-yet unidentified pathway at higher concentrations of NSC745885

Figure 6C:
FIG. 6C shows the attenuation of p53 and p21 degradation after treatment of proteasome inhibitor MG132 at lower concentration of NSC745885.

In FIG. 6C, HeLa cells were treated with the indicated concentrations of NSC745885 for 12 hours; proteasome inhibitor MG132 (1 uM or 10 uM) was added 3 hours before harvesting. Cell protein extracts were tested with anti-p53 and anti-p21 antibodies. The results are representative of two independent experiments. Proteasome inhibitor MG132 was able to attenuate the degradation of p53 and p21 by NSC745885, but only at lower concentrations of NSC745885 (FIG. 6C, compare lanes 2, 6, and 10). The assay indicates that NSC745885 decreases p53 and p21 protein levels by increasing their degradation, especially at lower doses.

Embodiment 8: NSC745885 Interacts with Zac1 in the Regulation of p53-dependent Activation in HeLa Cell HeLa and HeLa/shp53 cells were grown in DMEM supplemented with 10% charcoal/dextran-treated fetal bovine serum. Cells in a 24-well plate were transfected with jetPEI (PolyPlus-transfection, France) according to the manufacturer's protocol; total DNA was adjusted to 1.0 μg by the addition of empty vector DNA. Luciferase assays were performed using the Promega Luciferase Assay kit, and the measurement was expressed numerically as relative light units (RLU). Luciferase activities were presented as means and standard deviation of two transfected sets. Since the expression of many control vectors for monitoring transfection efficiency has been shown to be greatly affected by Zac1 (for example, Zac1 has been shown to enhance β-gal reporter gene expression approximately 6-8-fold), internal controls were not used. Instead, the reproducibility of the observed effects on luciferase activity was determined in multiple independent transfection experiments.

HeLa cells infected with human papillomavirus and expressing the E6 oncoprotein, which maintains endogenous wild-type p53 at a very low concentration, are used as a model system for studying human cervical tumorigenesis. In order for us to confirm the effects of DXR and NSC745885 on endogenous p53, HeLa cells were transiently transfected with a p53-dependent reporter (pG13-LUC) (FIG. 7A) and a p21 promoter reporter (p21-LUC) (FIG. 7B), along with an expression vector for a well-known p53 activator (Zac1). NSC745885 enhanced pG13-LUC reporter activity in a concentration-dependent manner, similar to DXR (FIG. 7A, closed columns).

Figure 7A:
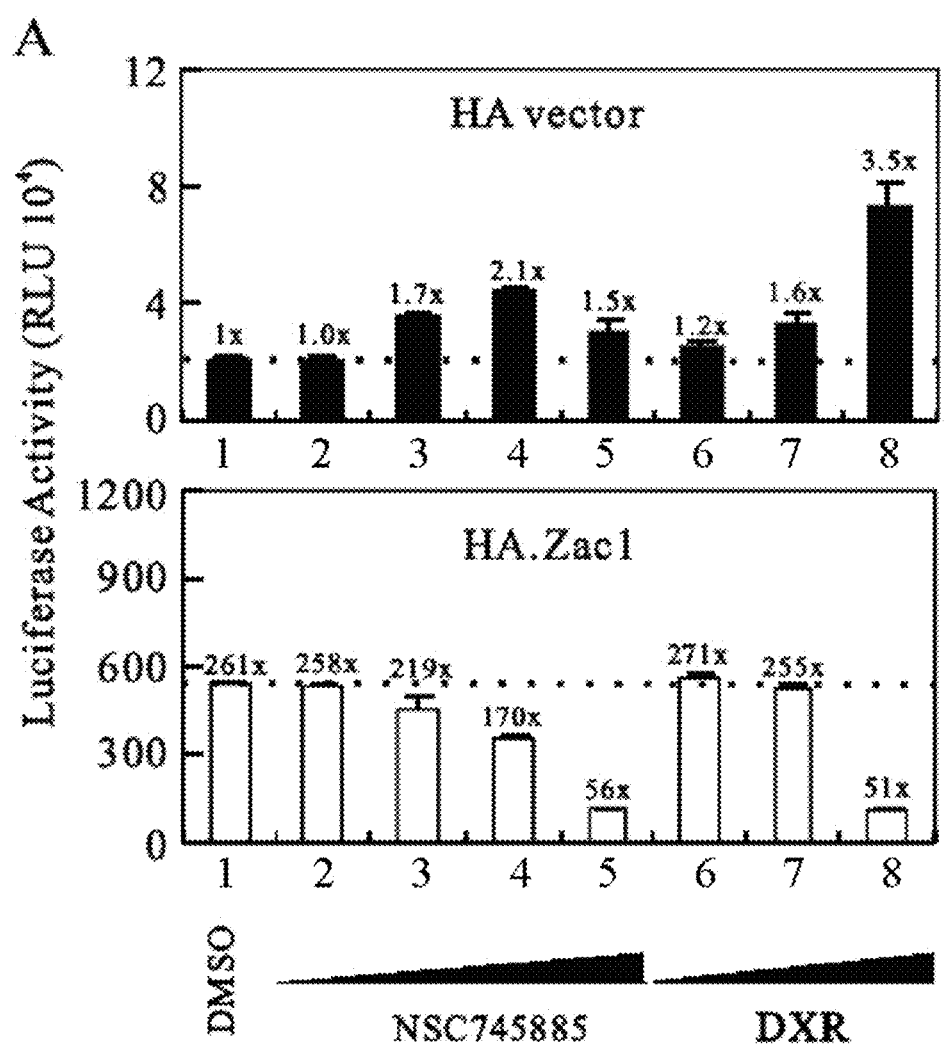
FIG. 7A shows the confirmation of Hela cells transiently transfected with a p53-dependent reporter (pG13-LUC).
Figure 7B:
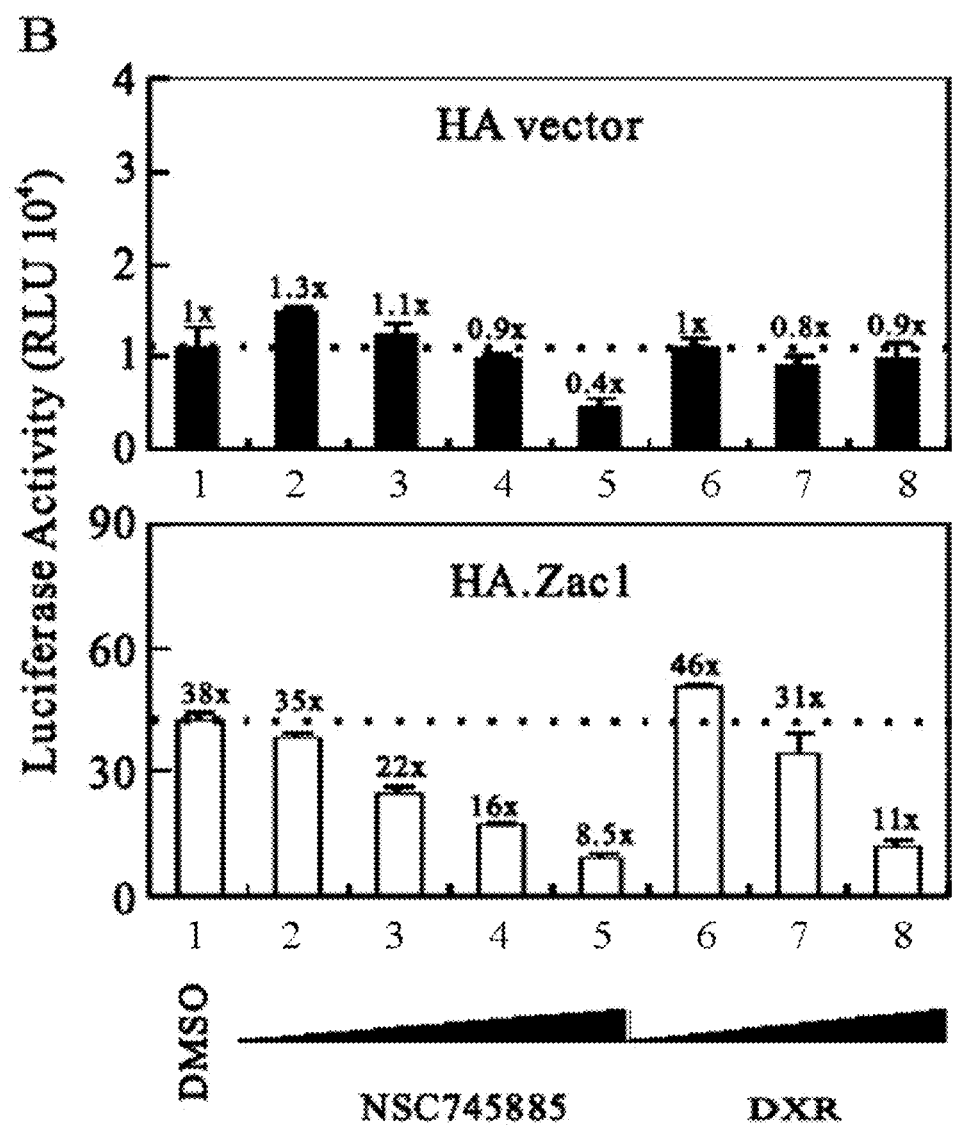
FIG. 7B shows the confirmation of Hela cells transiently transfected with a p21 promoter reporter (p21-LUC).

The assay suggested that Zac1 had a synergistic effect on p53-dependent transcriptional activation, whereas NSC745885 and DXR inhibited Zac1-induced activity (FIG. 7A, open columns). Similar patterns in p21 promoter reporter activity were observed (FIG. 7B). At the highest concentration, NSC745885 decreased p21 promoter reporter activity (FIG. 7B, compare histograms 1, 5 closed columns).

Embodiment 9: NSC745885 Cytotoxicity is Disrupted by p53

Figure 8:
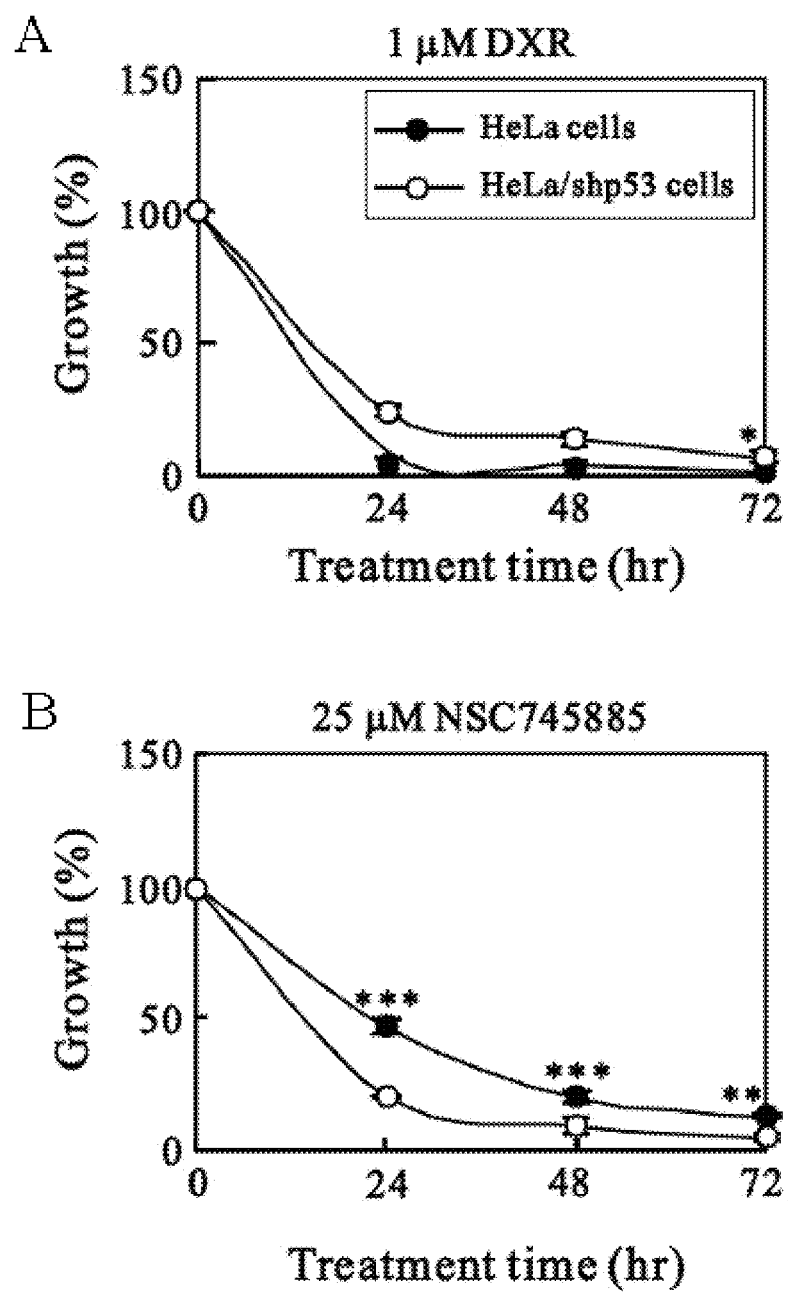
FIG. 8 (Panels A & B) shows an exemplary MTT assay result of NSC745885 treating HeLa and HeLa/shp53 cell.

To understand the functional role that endogenous p53 plays in the cytotoxic effects of DXR and NSC745885, we measured cell viability of HeLa or HeLa/shp53 cells using MTT cell viability assay. In this assay, endogenous p53 is silenced, both in the presence or absence of the drugs (FIG. 8). HeLa/shp53 cell is one of the cell lines included in NCI 60 platform. The sensitivity towards NSC745885 was significantly enhanced in HeLa/shp53 cells, which lack endogenous p53 (FIG. 8, Panel B, *, P<0.001 at 24 hours; *, P<0.001 at 48 hours; **, P=0.002 at 72 hours). Compared with the FIG. 6A, these results raise the interesting possibility that degradation pathways for p53 or other proteins are induced by NSC745885.

In a parallel experiment, DXR was dependent on endogenous p53 for cell killing. In this case, the status of p53 determines the DNA damage effects by 1, 2-heteroannelated anthraquinones; this effect was significant after long-term treatment (72 hours) (FIG. 8, Panel A, P=0.067 at 24 hours; P=0.760 at 48 hours; and *P=0.046 at 72 hours). The NSC745885 analyzed in the current study share the same anthraquinone core, but have different 1,2-heterocyclic moieties, which might mediate differential effects on cellular target molecules such as p53.

The Following Embodiments 10~12 are Performed with Bladder Cancer and other Cell Lines (T24, TSGH8301, MBT2 and J82)

Figure 9G:
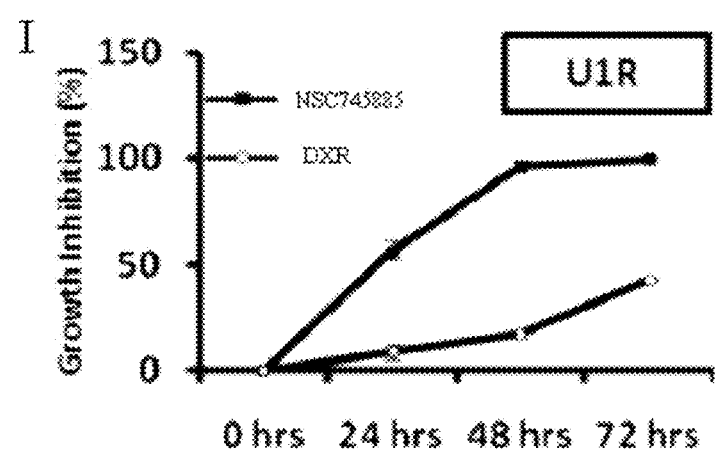
FIG. 9G shows the cell proliferation inhibiting ability of NSC745885 in anti-Doxorubicin cell line U1R.

Embodiment 10: The Cell Proliferation Inhibitory Effect of NSC745885 in Cancer Cell Lines To investigate the cell proliferation inhibition effect of NSC745885 in cancer cells, we compared the cancer cell proliferation inhibition effect of the NSC745885 with well-know bladder anti-cancer agent "Emodin" and clinical cancer chemical therapy agent "Doxorubicin". The experiment bladder cancer cell lines includes T24 (FIG. 9A, 9D) and MBT2 (FIG. 9 B, 9E). We also confirm the NSC745885 cell toxicity using the non-cancer cell fibroblast 3T3 (FIG. 9C) and normal epithelial cell SV_UC_1 (FIG. 9F). These experiment results demonstrate that NSC745885 (2.5 uM) possesses the distinct cancer cell proliferation inhibition ability, similar to the anticancer agent "Emodin" (40 uM) and "Doxorubicin". Furthermore, the NSC745885 has no cell toxicity in the normal cell. In addition, we also tested the cell proliferation inhibiting ability of NSC745885 in anti-Doxorubicin cell line U1R (FIG. 9G), the result shows NSC745885 has distinct the cell proliferation inhibiting ability. Therefore, these data show NSC745885 compound is an important anti-cancer inhibitor.

Embodiment 11: NSC745885 Down-regulates Oncogenic Stem Cell Factor (SCF)

Stem Cell Factor (also known as SCF, kit-ligand, KL, or steel factor) is a cytokine that binds to the c-Kit receptor (CD117). SCF can exist both as a transmembrane protein and a soluble protein. This cytokine plays an important role in hematopoiesis (formation of blood cells), spermatogenesis, and melanogenesis.

SCF plays an important role in the hematopoiesis during embryonic development. In the organs where hematopoiesis takes place, such as the fetal liver and bone marrow, all express SCF. SCF-deficient mice die in uterus from severe anemia. Mice that do not express the receptor for SCF (c-Kit) also die from anemia. SCF may serve as guidance cues to direct hematopoietic stem cells (HSCs) to their stem cell niche (the microenvironment in which a stem cell resides), and it plays an important role in HSC maintenance. Non-lethal point mutants on the c-Kit receptor can cause anemia, reduce fertility, and pigmentation.

During development, the presence of the SCF also plays an important role in the localization of melanocytes, which produce melanin and control pigmentation. In melanogenesis, melanoblasts migrate from the neural crest to their appropriate locations in the epidermis. Melanoblasts express the Kit receptor, and it is believed that SCF guides these cells to their terminal locations. SCF also regulates survival and proliferation of fully differentiated melanocytes in adults.

Figure 10:
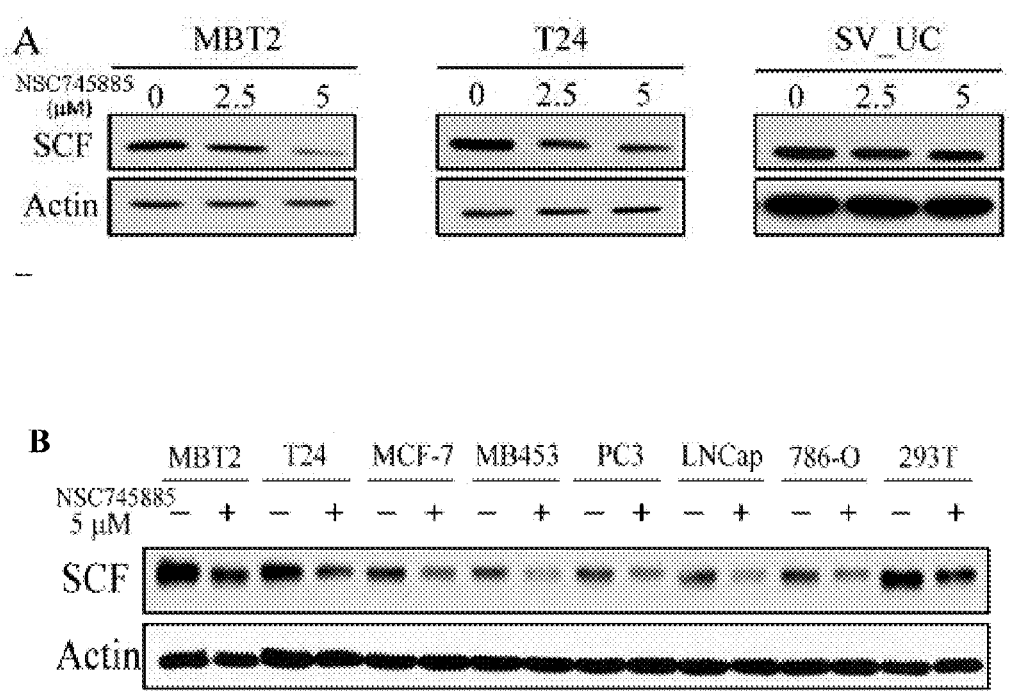
FIG. 10 shows NSC745885 down-regulates oncogenic stem cell factor (SCF).

To investigate whether NSC745885 down-regulates SCF in cancer cells, we treated bladder cancer cell (MBT2, T24) and normal epithelial cell (SV_HUC_1) with NSC745885 for 24 hours and then analyzed the SCF protein level. As shown in FIG. 10, Panel A, the SCF protein expression is suppressed with gradient increase of the concertinos of NSC745885.

We investigated NSC745885's effect on SCF expression in different cancer cells, including bladder cancer (MBT2, T24), breast cancer (MCF-7, MDA-MB-453), prostate cancer (PC3, LNCaP), kidney cancer (786-O), and kidney epithelial cell (293T). We treatment these different cancer cells with (+) or without (−) the NSC745885 (5 µM), and then analyzed SCF protein level. As shown in FIG. 10, Panel B, SCF level is significantly decreased by NSC745885 in all cell lines. These result demonstrate that the NSC745885 can inhibitor the SCF protein expression and inhibit the cancer cell proliferation.

The Following Embodiments 13-15 Demonstrated in Different Kinds of Cancer Cell

Embodiment 13: Cytotoxicity and Anti-cancer Activity of NSC745885 in vitro Screening NSC745885 was studied as a prototype for anti-proliferative activity against human cancer cell lines in NCI Drug Screen Program (Table 1, below). NSC745885 was evaluated in the full panel of human tumor cell lines derived from nine cancer cell types (leukemia, non-small cell lung cancer, colon cancer, CNS cancer, prostate cancer, melanoma, ovarian cancer, renal cancer and breast cancer). Each subpanel uses several cell lines and dose-response curves were drawn against the decadic logarithm (log 10) of the corresponding drug concentrations for each cell line by the subpanel group. They were also evaluated in the 60 cell line panel and anticancer assay was performed in accordance with the protocol of developmental therapeutics program (one dose mean graph). Results for each compound were reported as the proliferation percentage of the treated cells with that of the untreated control cells being 100. The proliferation percentage values at a drug dose of $10^{-5}$M for the 60 cancer cell lines are shown in Table 1. For each of these parameters the averaged values of mean graph midpoint (MG_MID) were calculated.

TABLE 1

Cytotoxicity of NSC 745885 at NCI in vitro 60-cell Drug Screen Program

| Panel/cell line | NSC 745885/proliferation percentage |
|---|---|
| Non-small cell lung cancer | |
| A549/ATCC | 104.18 |
| EKVX | 103.18 |
| HOP-62 | −100.00 |
| HOP-92 | — |
| NCI-H226 | 97.80 |
| NCI-H23 | 16.07 |
| NCI-H322M | 125.82 |
| NCI-H460 | 77.41 |
| NCI-H522 | — |
| Colon cancer | |
| COLO 205 | 111.54 |
| HCC-2998 | −0.74 |
| HCT-116 | −50.00 |
| HCT-15 | 1.48 |
| HT29 | 116.95 |
| KM12 | 98.60 |
| SW-620 | 7.30 |
| Breast cancer | |
| BT-549 | — |
| HS 578T | −7.40 |
| MCF7 | −50.74 |
| MDA-MB-231/ATCC | −17.33 |
| MDA-MB-435 | −87.88 |
| MDA-MB468 | −73.17 |
| NCI/ADR-RES | −2.53 |
| T-47D | −45.52 |
| Ovarian cancer | |
| IGROV1 | −88.34 |
| OVCAR-3 | −15.47 |
| OVCAR-4 | −94.43 |
| OVCAR-5 | −20.07 |
| OVCAR-8 | −10.07 |
| SK-OV-3 | 100.70 |
| Leukemia | |
| CCRF-CEM | −30.81 |
| HL-60(TB) | −21.77 |
| K-562 | 49.61 |
| MOLT-4 | −40.09 |
| RPMI-8226 | −27.97 |
| SR | 4.96 |
| Renal cancer | |
| 786-0 | −25.98 |
| A498 | 130.09 |
| ACHN | −94.31 |
| CAK1-1 | 1.97 |
| RXF393 | 20.11 |
| SN12C | −73.27 |
| TK-10 | 96.99 |
| UO-31 | −79.30 |
| Melanoma | |
| LOX IMVI | −50.63 |
| M14 | 74.54 |
| MALME-3M | −71.54 |
| SK-MEL-2 | −73.16 |
| SK-MEL-28 | 15.47 |
| SK-MEL-5 | 8.52 |
| UACC-257 | −83.07 |
| UACC-62 | −82.32 |
| Prostate cancer | |
| DU-145 | 40.76 |
| PC-3 | — |
| CNS cancer | |
| SF-268 | 16.29 |
| SF-295 | 126.17 |
| SF-539 | −47.11 |
| SNB-19 | 78.98 |
| SNB-75 | 79.03 |
| U251 | −89.26 |
| Mean | 2.68 |
| Delta | 102.68 |
| Range | 230.09 |

As shown in Table 1, NSC745885 has shown significant cytotoxic activity and was subsequently selected for a 60-cell panel assay to determine 50% growth inhibition ($GI_{50}$), total growth inhibition (TGI) and 50% cell killing ($LC_{50}$). As a result, NSC745885 was found to have potent activity with $GI_{50}$ between 0.16-17.4 µmol/L (2.04 µmol/L mean); $LC_{50}$ as low as 0.99 µmol/L and TGI as low as 0.40 µmol/L. Results of the study extended the initial in vitro observation reported in the data above and confirmed the anticancer ability of NSC745885. In the cancer panel, leukemia, melanoma and ovarian cancer lines were particularly sensitive to NSC745885, while the non-small cell lung cancer lines, colon, CNS, renal, prostate and breast subpanels were less sensitive. It is unexpected since NSC745885 with heterocyclic thiadiazole tetracyclic-system has differences in cytotoxicity which might have a significant effect on their interaction with DNA. For leukemia HL-60(TB), NSC745885 exhibited $GI_{50}$ as low as 0.16 μmol/L, $LC_{50}$ as low as 0.99 μmol/L and TGI as low as 0.40 μmol/L.

Given the striking correlations between telomerase activity and proliferation capacity in tumor cells, we expected that analysis of tetracyclic analogues chromophore might yield further insight into designing better lead compounds for anti-cancer therapies.

TABLE 2

In vitro anticancer activity by NSC 745885 in the NCI's 60 human cancer cell lines

| Panel/cell line | NSC 745885 | | |
| --- | --- | --- | --- |
| | $GI_{50}$ (μmol/L) | TGI (μmol/L) | $LC_{50}$ (μmol/L) |
| Leukemia | | | |
| CCRF-CEM | 1.08 | 4.10 | >100 |
| HL-60(TB) | 0.16 | 0.40 | 0.99 |
| K-562 | 1.92 | 15.90 | 41.20 |
| MOLT-4 | 0.49 | 1.84 | 4.71 |
| RPMI-8226 | 1.18 | 3.46 | >100 |
| SR | — | — | — |
| Non-small cell lung cancer | | | |
| A549/ATCC | 14.70 | 36.60 | 91.00 |
| EKVX | 1.55 | 3.45 | 7.66 |
| HOP-62 | 1.28 | 3.31 | 8.53 |
| HOP-92 | 2.52 | 6.64 | >100 |
| NCI-H226 | 4.48 | 21.60 | 63.70 |
| NCI-H23 | 1.44 | 6.04 | >100 |
| NCI-H322M | 17.40 | 47.80 | >100 |
| NCI-460 | 3.27 | 14.30 | 47.30 |
| NCI-H522 | 1.66 | 3.93 | 9.31 |
| Colon cancer | | | |
| COLO 205 | 13.40 | 28.90 | 62.40 |
| HCC-2998 | 16.40 | 33.10 | 66.60 |
| HCT-116 | 1.93 | 5.40 | >100 |
| HCT-15 | 1.71 | 3.72 | 8.12 |
| HT29 | 13.40 | 50.40 | >100 |
| KM12 | 1.96 | 5.54 | 59.70 |
| SW-620 | 1.79 | 3.50 | 6.84 |
| CNS cancer | | | |
| SF-268 | 2.17 | 5.77 | 27.70 |
| SF-295 | 1.90 | 4.04 | 8.56 |
| SF-539 | 1.46 | 2.94 | 5.91 |
| SNB-19 | 2.28 | 5.82 | 26.00 |
| SNB-75 | 2.03 | 5.20 | 18.60 |
| U251 | 1.61 | 2.96 | 5.44 |
| Melanoma | | | |
| LOX IMVI | 0.82 | 2.13 | 4.86 |
| MALME-3M | 1.66 | 3.15 | 5.96 |
| M14 | 2.15 | 4.85 | >100 |
| MDA-MB-435 | 1.91 | 3.31 | 5.76 |
| SK-MEL-2 | 1.68 | 4.22 | 22.50 |
| SK-MEL-28 | 1.85 | 3.38 | 6.18 |
| SK-MEL-5 | 1.58 | 2.92 | 5.41 |
| UACC-257 | 1.74 | 3.51 | 7.09 |
| UACC-62 | 1.45 | 2.90 | 5.79 |

TABLE 2-continued

In vitro anticancer activity by NSC 745885 in the NCI's 60 human cancer cell lines

| Panel/cell line | NSC 745885 | | |
| --- | --- | --- | --- |
| | $GI_{50}$ (μmol/L) | TGI (μmol/L) | $LC_{50}$ (μmol/L) |
| Ovarian cancer | | | |
| IGROV1 | 1.36 | 2.94 | 6.35 |
| OVCAR-3 | 0.55 | 2.46 | 11.10 |
| OVCAR-4 | 0.65 | 2.17 | 5.57 |
| OVCAR-5 | 1.91 | 4.11 | 8.84 |
| OVCAR-8 | 1.66 | 4.68 | 59.80 |
| NCI/ADR-RES | 1.86 | 12.60 | >100 |
| SK-OV-3 | 7.71 | 22.50 | 53.40 |
| Renal cancer | | | |
| 786-0 | 6.17 | 19.30 | 50.40 |
| A498 | 12.40 | 25.40 | 52.00 |
| ACHN | 1.46 | 2.77 | 5.27 |
| CAK1-1 | 1.61 | 2.96 | 5.44 |
| RXF393 | 1.75 | 4.40 | 14.60 |
| SN12C | 1.33 | 3.17 | 7.56 |
| TK-10 | 2.85 | 10.90 | 50.40 |
| UO-31 | 1.62 | 3.12 | 6.01 |
| Prostate cancer | | | |
| PC-3 | 3.23 | >100 | >100 |
| DU-145 | 1.67 | 3.24 | 6.27 |
| Breast cancer | | | |
| MCF7 | 1.53 | 3.34 | 7.29 |
| MDA-MB-231/ATCC | 1.75 | 5.90 | >100 |
| HS 578T | 1.41 | 5.02 | 56.00 |
| BT-549 | 1.63 | 3.13 | 6.01 |
| T-47D | 1.39 | 3.39 | 8.27 |
| MDA-MB-468 | — | — | — |

Figure 11:
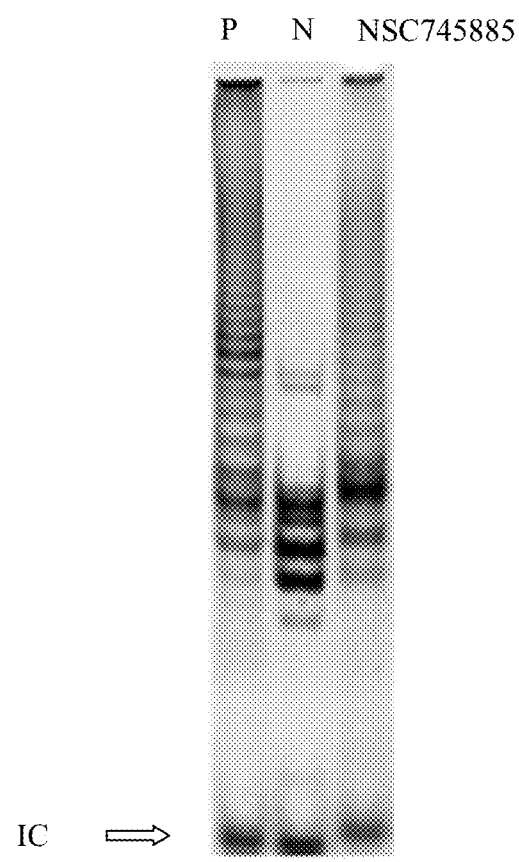
FIG. 11 shows inhibition of telomerase activity by NSC745885 in lung cancer cell line H1299 cells.

Embodiment 14: Inhibition of Telomerase Activity by NSC745885 in Lung Cancer Cell Line H1299 Cells Binding of low-molecular weight ligands to quadruplexes was first studied with the classic DNA intercalator ethidium and the telomere sequence T4G4 from Oxytricha. It is apparent that G-quadruplexes, with their unique structural, electrostatic and hydrogen bonding features, are the more likely targets for drug action rather than typical duplex or triplex DNA. However, the G-quadruplex inhibitors have at least some affinity for duplex DNA, and thus, tend to exhibit conventional cytotoxicity, as well as particular telomerase-associated properties. To evaluate the effects of these derivatives on telomerase inhibition, we used PCR-based telomerase assay and TRAP (telomeric repeat amplification protocol) assay at a compound concentration of 100 μM. The telomerase activity result demonstrate that the NSC745885 lane shape has little different from positive control (P, no inhibitor) and negative control (N, RNase A-treated cell extract, no inhibitor) FIG. 11. The telomerase inhibitory data available here for tetracyclic anthraquinone system (NSC745885) have demonstrated that activity at the micromolar level can be achieved with pharmacologically acceptable compounds.

Embodiment 15: Repressing Effects of NSC745885 on Tumor Size in Oral Cancer Cell (SAS Cells).

Figure 12:
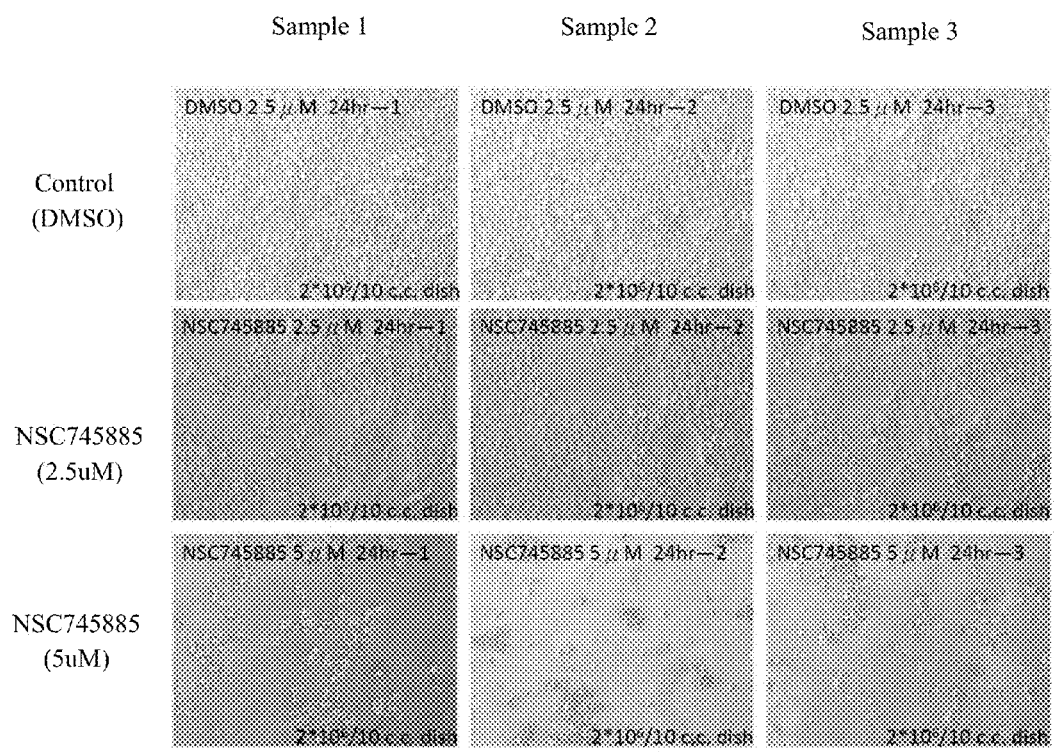
FIG. 12 shows exemplary morphological variations of SAS cells treated with NSC745885.
Figure 13:
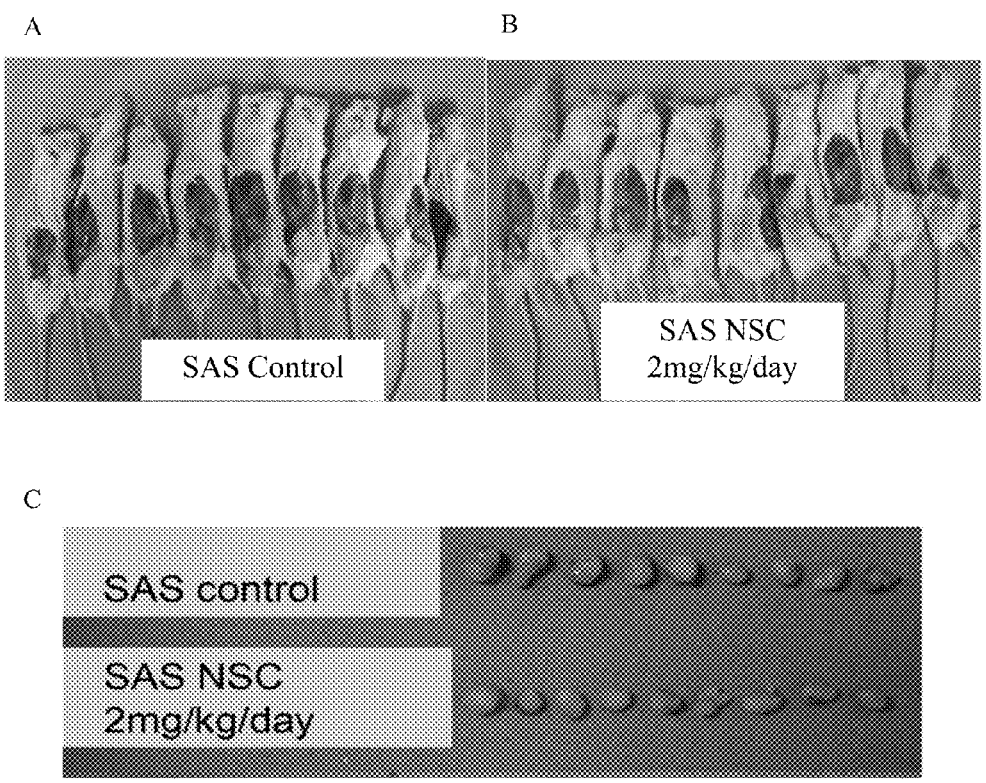
FIG. 13 shows repressing effects of NSC745885 on tumor size in oral cancer cell (SAS cells). Panel A shows the control group administered with PBS (Control). Panel B shows the control group administered with NSC745885 (2 mg/kg/day). Panel C shows the tumor tissues isolated from both groups.
Figure 14A:
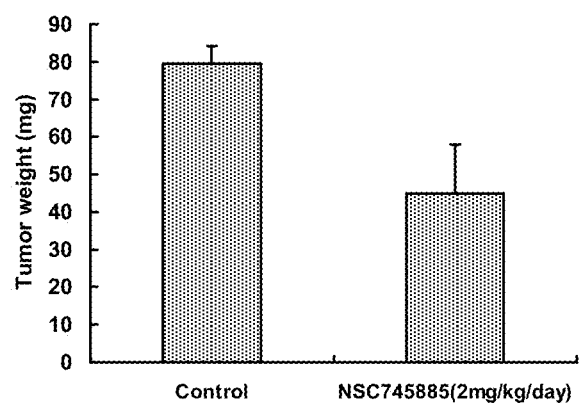
FIG. 14A shows the statistical result of the repressing effects of NSC745885 on weight of the isolated tumor tissues in oral cancer cell (SAS cells).
Figure 14B:
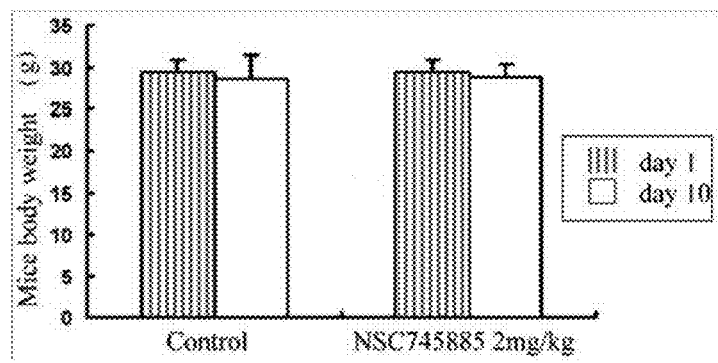
FIG. 14B shows the effect of NSC745885 on the body weight of the mice, on which the tumor tissues were xenographed and later isolated.

Morphological variations of SAS cells treated with 0, 2.5, and 5 uM NSC745885 for 24 hours are shown in FIG. 12. In all three testing samples, at both doses of 2.5 uM and 5 uM, NSC745885 can significantly inhibit the SAS cells proliferation in 24 hours. Furthermore, we tested the effects of NSC745885 on tumor size in mouse. This experiment had two animal groups: one is administered after tumor xenograft transplantation with PBS (Control, FIG. 13, Panel A) and the other with NSC745885 (2 mg/kg/day, FIG. 13, Panel B). The mice were euthanized after 10 days and the tumor tissues were immediately isolated. The result shows that the tumor size was reduced with increased NSC745885 concentration compared with control group. (FIG. 13, Panel C). The result indicated that tumor sizes (FIG. 14A) in the test subjects were reduced and the body weight (FIG. 14B) was not significantly decreased in the group treated with NSC745885 (2 mg/kg/day). The result shows that the NSC745885 can significantly inhibit tumor proliferation with no side effects on body weight.

A pharmaceutical composition having a NSC745885 as an effective component can be formulated into various forms suited for the purpose of the treatment, by a conventional method using pharmaceutically acceptable carriers, diluents, or the like. Examples of such forms of pharmaceutical compositions include solid formulations such as tablets, pills, dispersible powders, granules, capsules, and suppositories, liquid formulations such as injections, suspensions, syrups, and emulsions, and semi-solid formulations such as plasters.

The amount of a NSC745885 used in a pharmaceutical composition as an effective component for treatment of humans can be, for example, 100 to 500 mg (approximately 90 to 95% by weight of the composition) for a tablet or capsule if a commercially available NSC745885 or a purified preparation is used.

The dosage of a NSC745885 used in a pharmaceutical composition can conveniently be determined as a function of the intended treatment, the nature of the condition being treated. For example, the dosage for adult humans can be in the range of about 500 to 2000 mg per day as the amount of effective chemical component, but it is not so restricted. Furthermore, the abovementioned lyophilized 0/W emulsion can appropriately be used as a formulation or as a material for formulations.

Various additives conventionally used in formulations can be advantageously incorporated in the pharmaceutical formulation of the present invention so long as the additives do not inhibit the desired action of the NSC745885. Moreover, a telomerase or a cellular proliferation inhibitor as well as an apoptosis inducer of the present invention could be rendered even more effective in the treatment of cancer by the co-administration of a chemotherapeutic agent (anticancer agent) to the cancer cells being attacked by the present invention.

While specific embodiments have been described in detail in the foregoing detailed description, it will be appreciated by those skilled in the art that various modifications and alternatives to those details could be developed in light of the overall teachings of the disclosure and the broad inventive concepts thereof. It is understood, therefore, that the scope of the present invention is not limited to the particular examples and implementations disclosed herein, but is intended to cover modifications within the spirit and scope thereof as defined by the appended claims and any and all equivalents thereof.

What is claimed is:

1. A method for treating cancer in a mammalian subject in need thereof, consisting of:
   inducing apoptosis, inhibiting cancer cell proliferation, or inhibiting telomerase activity in cancer cells of the mammalian subject by administering to the mammalian subject an effective amount of a pharmaceutical composition comprising:
   a compound having the formula (I):

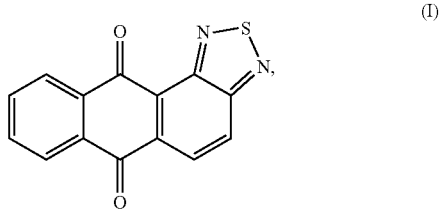 [SMILES: O=C1c2ccccc2C(=O)c2c1ccc1nsnc21]

or pharmaceutically acceptable salts thereof; and
   a pharmaceutically acceptable carrier, a diluent, an excipient, or a combination thereof.

2. The method of claim 1, wherein the cancer is selected from the group consisting of a lung cancer, a hepatic cancer, a bladder cancer, a breast cancer, a prostate cancer, a kidney cancer, an oral cancer, a cervical cancer and an ovarian cancer.

3. A method for inducing apoptosis in a mammalian cancer cell comprising the step of:
   administering to the mammalian cancer cell an effective amount of a pharmaceutical composition comprising: anthra[2,1-c][1,2,5]thiadiazole-6,11-dione, or pharmaceutically acceptable salts thereof; and a pharmaceutically acceptable carrier, a diluent, an excipient, or a combination thereof.

4. The method of claim 3, wherein the cancer cell is selected from the group consisting of a lung cancer cell, a hepatic cancer cell, a bladder cancer cell, a breast cancer cell, a prostate cancer cell, a kidney cancer cell, an oral cancer cell, a cervical cancer cell and an ovarian cancer cell.

5. A method for inhibiting proliferation of a mammalian cancer cell, comprising the step of:
   administering to the cancer cell an effective amount of a pharmaceutical composition comprising: anthra[2,1-c][1,2,5]thiadiazole-6,11-dione, or pharmaceutically acceptable salts thereof;
   and a pharmaceutically acceptable carrier, a diluent, an excipient, or a combination thereof.

6. The method of claim 5, wherein the cancer cell is one selected from the group consisting of a lung cancer cell, a hepatic cancer cell, a bladder cancer cell, a breast cancer cell, a prostate cancer cell, a kidney cancer cell, an oral cancer cell, a cervical cancer cell and an ovarian cancer cell.

7. A method for inducing apoptosis in one or more cancer cells of a mammalian subject, comprising the step of:
   administering to the subject a biologically active amount of a pharmaceutical composition comprising:
   anthra[2,1-c][1,2,5]thiadiazole-6,11-dione, or pharmaceutically acceptable salts thereof; and
   a pharmaceutically acceptable carrier, a diluent, an excipient, or a combination thereof.

8. The method of claim 7, wherein the one or more cells are selected from the group consisting of lung cancer cells, hepatic cancer cells, bladder cancer cells, breast cancer cells, colon cancer cells, pancreatic cancer cells, prostate cancer cells, kidney cancer cells, oral cancer cells, cervical cancer cells and ovarian cancer cells.

9. A method for inhibiting cancer cell proliferation in a mammalian subject comprising the step of:
   administering to one or more cancer cells in the subject a biologically active amount of a pharmaceutical composition comprising:
   anthra[2,1-c][1,2,5]thiadiazole-6,11-dione, or pharmaceutically acceptable salts thereof; and
   a pharmaceutically acceptable carrier, a diluent, an excipient, or a combination thereof.

10. The method of claim 9, wherein the one or more cells are selected from the group consisting of lung cancer cells, hepatic cancer cells, bladder cancer cells, breast cancer cells, colon cancer cells, pancreatic cancer cells, prostate cancer cells, kidney cancer cells, oral cancer cells, cervical cancer cells and ovarian cancer cells.

11. A method for inhibiting a telomerase enzyme's enzymatic activity in a mammalian subject, said method comprising the step of:

exposing the telomerase of said mammalian subject to a biologically active amount of a pharmaceutical composition comprising:

anthra[2,1-c][1,2,5]thiadiazole-6,11-dione, or pharmaceutically acceptable salts thereof; and a pharmaceutically acceptable carrier, a diluent, an excipient, or a combination thereof.

* * * * *